United States Patent [19]

Reese

[11] Patent Number: 4,750,481
[45] Date of Patent: Jun. 14, 1988

[54] OSTEOTOMY APPLIANCES AND METHOD

[76] Inventor: H. William Reese, 1450 S. Dobson, Suite 201, Mesa, Ariz. 85202

[21] Appl. No.: 866,337

[22] Filed: May 23, 1986

Related U.S. Application Data

[62] Division of Ser. No. 601,069, Apr. 16, 1984, Pat. No. 4,627,425.

[51] Int. Cl.$^4$ .............................................. A61F 5/04
[52] U.S. Cl. .............................. 128/92 VY; 128/92 V
[58] Field of Search .......... 128/92 XY, 92 VY, 92 V, 128/303 R, 305

[56] References Cited

U.S. PATENT DOCUMENTS

| | | | |
|---|---|---|---|
| 4,335,715 | 6/1982 | Kirkley | 128/92 VY |
| 4,440,168 | 4/1984 | Warren | 128/92 VY |
| 4,501,268 | 2/1985 | Comparetto | 128/92 VY |
| 4,565,191 | 1/1986 | Slocum | 128/92 VY |
| 4,627,425 | 12/1986 | Reese | 128/92 VY |

Primary Examiner—C. Fred Rosenbaum
Assistant Examiner—H. Macey
Attorney, Agent, or Firm—Cahill, Sutton & Thomas

[57] ABSTRACT

Osteotomy appliance and method for correcting bone deformities. The appliance comprises a guide to be used by the surgeon to make a second cut in a bone in predetermined angular relationship to a first cut in the bone. In one type of osteotomy the method and appliance enable a precise wedge-shaped piece of bone to be excised, leaving perfectly mating surfaces on the bone segments to be reunited. The guide has associated therewith a follower adapted to be placed in the first saw cut. The guide is adjustable positioned in relation to the follower to guide the second saw cut in the desired position. The method involves creating a hole in the bone at approximately the apex of the bone piece to be removed and utilizing pin members disposed in the hole for positioning guides for the first and second saw cuts.

5 Claims, 2 Drawing Sheets

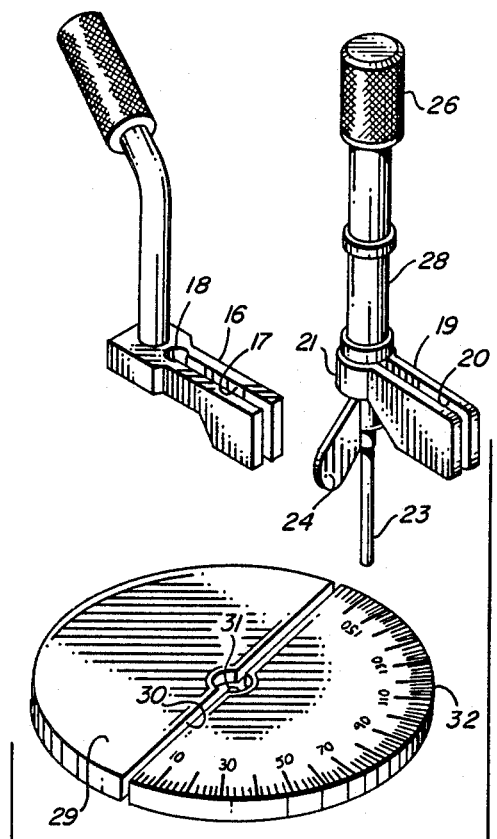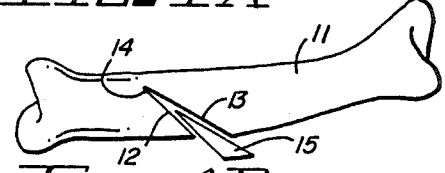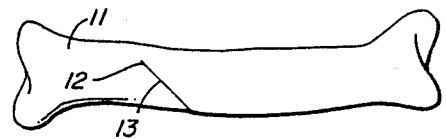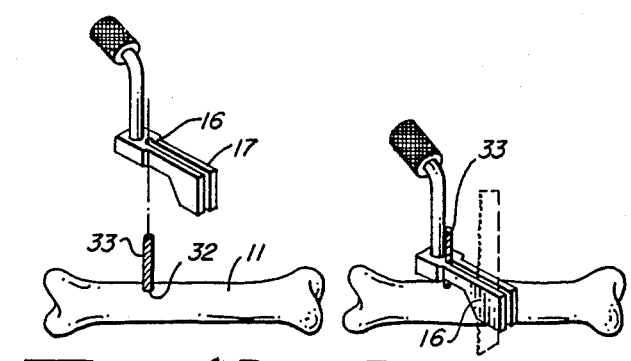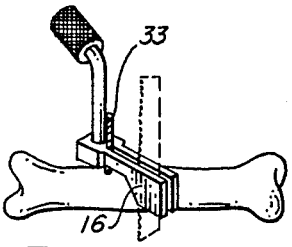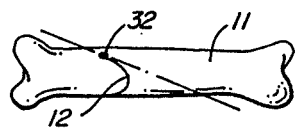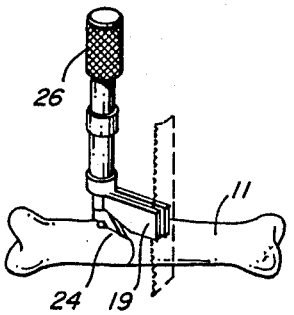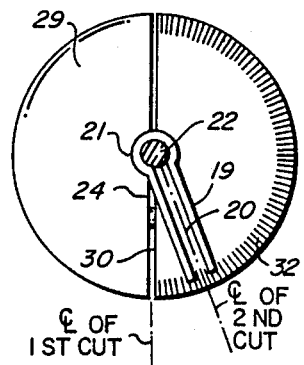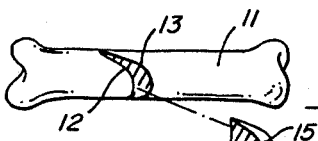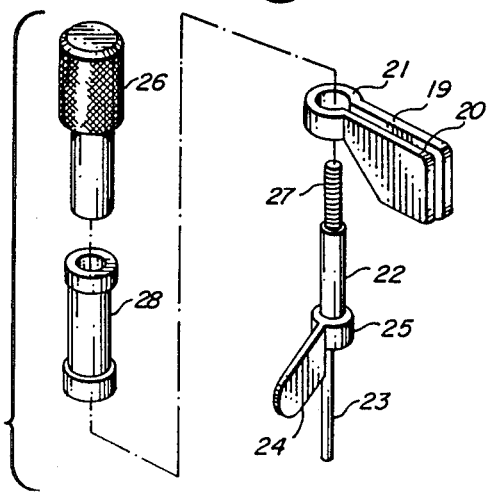

OSTEOTOMY APPLIANCES AND METHOD

This is a division of application Ser. No. 601,069, filed Apr. 16, 1984, now U.S. Pat. No. 4,627,425 granted Dec. 9, 1986.

TECHNICAL FIELD

This invention is useful in surgical procedures in which a pair of intersecting saw cuts are made in a human bone to separate or excise a portion of the bone.

BACKGROUND ART

The most common osteotomy requiring the accurate placement and execution of a pair of intersecting cuts is that performed to correct longitudinal angular deformity of a bone. In this operation a wedge-shaped segment of the bone is removed and the remaining segments repositioned to bring their severed surfaces together to realign the bone longitudinally. To insure correct realignment of the bone, it is essential that the saw cuts performed to remove the wedge-shaped segment be accurately placed with respect to each other. The saw cuts also are required to be planar so that when the severed end regions of the remaining bone segments are brought into contact their surfaces mate uniformly across the severed surfaces to promote rapid and structurally effective mending, or knitting, of the bone. These two requirements for the saw cuts suggest the desirability of employing a guide or guides for the osteotome, or saw, when the cuts are being made in the bone.

U.S. Pat. No. 4,335,715 granted June 22, 1982 to W. H. Kirkley for "Osteotomy Guide" discloses apparatus in which a pair of pins positioned on an arcuate track are inserted into the bone to serve as a guide for the surgeon in making cuts to derotate a bone or to excise a section thereof. The guide device and method disclosed in this patent gives only a general indication of where the surgeon is to make the saw cuts and if, for example, one saw cut is misplaced, the device in no way assures that the second cut will be properly positioned in relation to the first cut.

U.S. Pat. No. 4,349,018, granted Sept. 14, 1982 to G. R. Chambers for "Osteotomy Apparatus" discloses a fairly complex assemblage for guiding saw cuts to be made during a proximal tibia osteotomy or a total knee replacement operation. The apparatus there disclosed and its method of use would be totally unsuitable for osteotomies on more fragile and delicate bones such as are found in the foot and the hand.

There is a need, therefore, for an appliance and a method which will enable a surgeon performing an osteotomy to precisely locate and effect intersecting saw cuts in a bone, particularly a small bone of the hand or foot.

DISCLOSURE OF THE INVENTION

The implements of this invention comprise a set of appliances the most important of which is a guide arrangement for assisting the surgeon in locating and performing the second saw cut of the pair of cuts to be made. This appliance includes a follower adapted to be positioned within the first saw cut and a saw guide movably positionable with respect to the follower and adapted to be set and held in a position to guide the saw for the second cut. The appliance set may, if desired, also include a protractor device to assist in precisely setting the angular relationship between the guide for the second saw cut and the follower.

The method of this invention contemplates drilling or otherwise forming a hole in the bone at the approximate location of the intersection between the two saw cuts to be made in the bone. Pin means are inserted into this hole and serve as means for positioning the guides utilized in making both the first and second saw cuts. This hole and pin technique, when employed in conjunction with saw guides having fairly broad faces for maintaining the position of the saw, insures that two planar cuts will be made which will be perfectly mated when the bone is adjusted.

BRIEF DESCRIPTION OF THE DRAWINGS

FIGS. 1A through 1C illustrate the manner in which an angulational osteotomy can be employed to correct a longitudinal orientation deformity in a bone;

FIG. 2 is a perspective view of one set of appliances constructed in accordance with this invention;

FIG. 3 is an exploded view of an appliance guide for making the second saw cut of an osteotomy;

FIGS. 4A through 4F illustrate the method of performing an osteotomy according to this invention and utilizing one of the appliances of this invention;

BEST MODE FOR CARRYING OUT THE INVENTION

Figure 5:
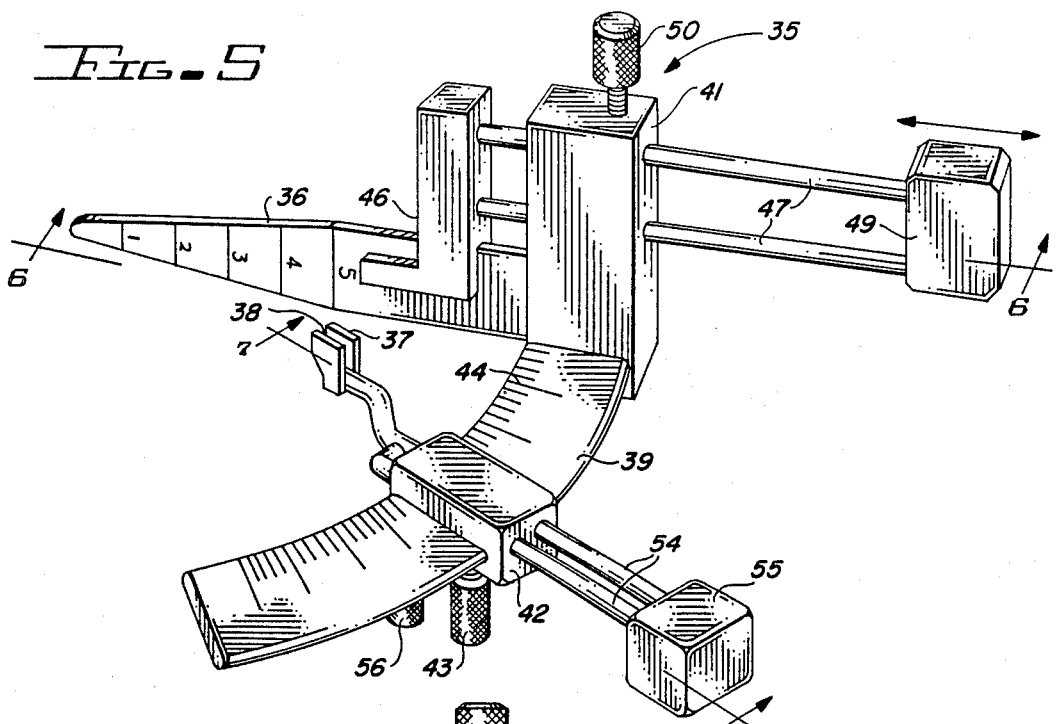
FIG. 5 is a perspective view of another appliance set constructed in accordance with this invention.

FIGS. 1A through 1C illustrate the steps followed in a conventional angulation osteotomy performed to correct an angular longitudinal deformity in a bone. In this example, the bone, designated by reference numeral 11, through abnormal growth or accident, has one end thereof displaced from what would normally be the longitudinal axis of the bone. The first step performed by the surgeon is a saw cut 12 made obliquely with respect to the normal longitudinal axis of the bone (FIG. 1A). A second saw cut 13 is next made in a bone 11 at an angle to the first saw cut 12, so that the cuts intersect at an apex 14. Saw cuts 12 and 13 separate from the bone a wedge-shaped section 15 which is excised from the remaining bone sections (FIG. 1B). The surgeon next reforms the bone to bring together the facing planar surfaces of the remaining bone sections which were produced by saw cuts 12 and 13 (FIG. 1C). This brings the ends of the bone 11 into their proper relationship. If desired, a pin or screw (not shown) may be driven into the bone generally normal to the plane of the adjoining surfaces produced by saw cuts 12 and 13 to hold the bone sections together until the normal healing process causes the bone segments to knit together.

It can readily be understood that a successful osteotomy requires that saw cuts 12 and 13 in bone 11 be precisely located in angular relationship one to the other and that the saw cuts themselves be made with precision so as to produce planar mating surfaces at the severed regions of the remaining bone segments. The angle between saw cuts 12 and 13 determines the degree of correction to which the bone is subjected. The surgeon can determine this angle with some precision by measuring the deformity to be corrected. Obviously, the surgeon can place the saw cuts 12 and 13 with greater accuracy if he has an appliance to guide his saw blade when he makes these cuts. Similarly, such an appliance can assist the surgeon in producing planar, tightly mating cut surfaces which are most likely to produce a strong growth bond in the corrected bone structure.

This invention provides appliances for assisting the surgeon in the osteotomy and provides for a unique method of employing one of the appliances in the performance of the operation. FIG. 2 illustrates one of the appliances, or what may be termed a set of appliances, which embody this invention. These appliances are a first saw cut guide 16 having a slot 17 therein which opens to the distal end of the guide for receiving a microtome, or saw blade, not shown. Guide 16 has a cylindrical hole 18 which is adapted to receive a pin member, not shown, for positioning guide 16 adjacent a bone to be cut. Guide 16 further is provided with a handle protruding upwardly therefrom, by which the guide is manipulated by the surgeon.

The second appliance of this set is a second saw cut guide 19 which also has a slot 20 therein which opens to the distal end of the guide for receiving the osteotome. Guide 19 has a collar 21 at its proximal end which fits around a shaft 22 and which permits guide 19 to pivot or swing about shaft 22 (see FIG. 3). Shaft 22 has a pin-like extension depending coaxially therefrom, and a follower 24 mounted thereon by means of a collar 25. Collar 25 is tightly secured to shaft 22 so that follower 24 rotates with the shaft and supports collar 21 of guide 19. The relationship is such that the guide 19 is pivotally moveable with respect to follower 24 so that the angular relationship between these two members can be adjusted. Once the desired angular relationship between the slot 20 in guide 19 and the follower 24 has been established, collar 21 is clamped against collar 25 to maintain this relationship by a knurled nut 26 carried by the threaded upper end 27 of shaft 22. If desired, a sleeve 28 may be interposed between nut 26 and collar 21 of saw guide 19. Nut 26 and sleeve 28 also function as an upstanding handle for manipulating saw guide 19.

The last appliance of the set illustrated in FIG. 2 is a protractor means 29 for assisting the surgeon in setting a desired angular relationship between the slot 20 in saw guide 19 and follower 24. Protractor means 29 comprises a disc of rigid material, such as metal or plastic, having a follower positioning slot 30 extending diametrically across the protractor means and through a central hole 31 adapted to receive the pin-like extension 23 on saw guide 19. Protractor means 29 is also provided with angle indicia 32 radiating from and surrounding hole 31 at the periphery of the protractor. To set the relationship between saw guide 19 and follower 24, a surgeon places the saw guide on protractor means 29 with pin 23 in hole 31 and follower 24 in slot 30. The nut 26 on the saw guide 19 is loosened and saw guide 19 moves to the proper angular position with respect to follower 24 and nut 26 is thereafter tightened.

The method of utilizing the appliance set of FIG. 2 is illustrated in FIGS. 4A through 4F.

In preparation for making saw cuts 12 and 13 in the bone 11, the surgeon drills or otherwise forms a hole 32 in the bone 11 at approximately the apex, or intersection, of the two saw cuts to be made. Referring to FIG. 4A, this hole 32 may be formed by drilling with a bit 33. This hole 32 is adapted to receive a pin-like support member for the first saw cut guide 16, which pin member may in fact be the drill 33 which is simply left in place after the hole has been formed. The surgeon places first saw guide 16 in position adjacent the bone by sliding the guide onto bit 33 which is received in hole 18 of the guide. Positioning the guide 16 by means of its handle, and with the blade of the osteotome in the slot 17 of the guide 16 the surgeon then makes the first cut 12 in the bone as illustrated in FIG. 4B.

When cut 12 is completed, guide 16 and bit 33 are removed leaving bone 11 having the appearance shown in FIG. 4C.

Having determined the shape of the wedge-shaped section 15 to be excised from the bone, the surgeon sets the angular relationship which is to exist between saw cuts 12 and 13 by placing guide 19 on protractor means 29 and fixing the slot 20 in the proper angular relationship with follower 24 in the manner described above and which is illustrated in FIG. 4D.

The next step in the method of this invention involves placing the second saw cut guide 19 on bone 11 in such a manner that the pin-like extension 23 enters hole 32 in the bone 11 and the follower 24 is positioned within the first saw cut 12 which has been made in the bone 11. This positioning of guide 19 disposes the slot 20 therein to receive the blade of the osteotome to guide it in making a precise planar second cut 13 in bone 11 in proper relationship with the first cut 24 (see FIG. 4E).

Second saw guide 18 is thereafter removed from the bone 11 and the wedge-shaped section 15 which has been sawed free of the bone is removed and the bone thereafter reoriented in the manner described above. Removal of the wedge-shaped section of bone 15 is illustrated in FIG. 4F.

FIGS. 5 through 9 illustrate another embodiment of the invention in the form of an appliance, indicated generally by reference numeral 35, which offers features and advantages not possessed by the previously described embodiment. Appliance 35, like second saw cut guide 19 of the previous embodiment, is intended to assist the surgeon in precisely locating a second saw cut 13 in the performance of an osteotomy. Appliance 35 has a blade-like follower 36 which is adapted to be inserted into the first made saw cut 12. Appliance 35 further includes a second saw cut guide 37 which is moveably connected to follower 36 in such a manner that the angular relationship between an osteotome guide slot 38 in guide 37 and follower 36 can be adjusted by the surgeon. The adjustable connection between guide 37 and follower 36 is preferably provided by an arcuate track member 39.

Figure 6:
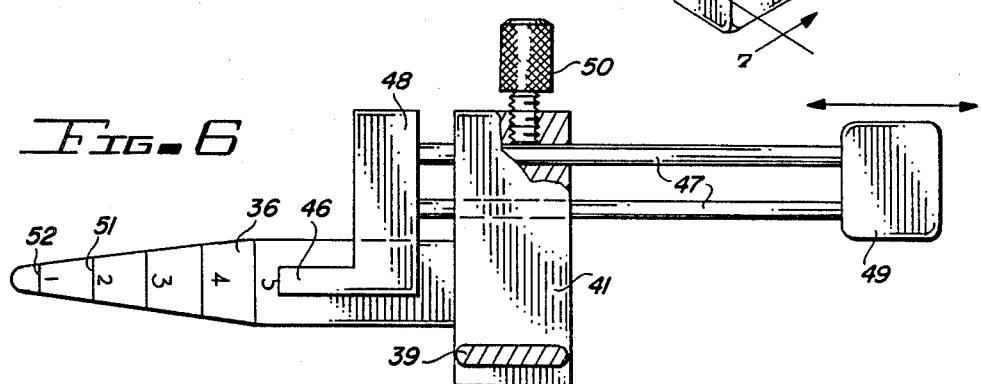
FIG. 6 is a vertical section view of the appliance of FIG. 5 taken generally as indicated by the line 6—6 in FIG. 5.
Figure 7:
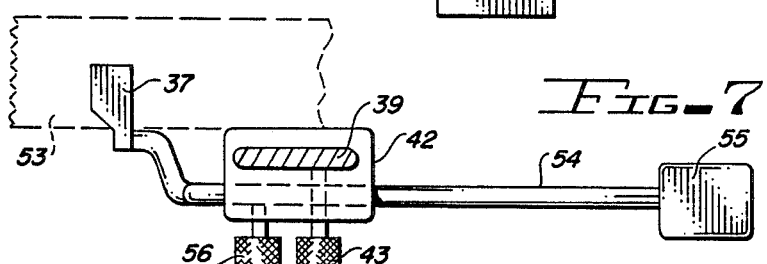
FIG. 7 is a vertical sectional view of the appliance of FIG. 5 taken generally as indicated by the line 7—7 in FIG. 5.

In the embodiment of appliance 35 shown in FIGS. 5 through 7, the follower 36 is secured to a pedestal 41, which is in turn fixedly secured to track 39. Guide 37 is mounted for arcuate sliding movement along track 39 by means of a follower 42 having a set screw 43 passing therethrough for engagement with track 39. Set screw 43 is loosened to permit the surgeon to move follower 42 along track 39 to set the angular relationship between the saw guide 37 and the follower 36. Once the proper angular relationship is established, screw 43 is tightened to hold the guide in this position. If desired, track 39 may have indicia 44 provided on the face thereof to assist the surgeon in establishing the desired angular relationship between blade 36 and guide 37. Indicia 44 preferably is in the form of markings of angular degrees so that track 39 functions as a protractor in setting the angular relationship between follower 36 and guide 37. It should be obvious that instead of fixedly mounting follower 36 to track 39 and having guide 37 moveable in relation thereto, that the guide 37 could be fixed to track 39 and blade 36 be mounted in such a manner as to be moveable along the track in relation to guide 37.

One of the features of appliance 35 is that it possesses means for assuring that the osteotomy, when performed, will leave intact bone cortex beyond the apex of the saw cuts. In other words, appliance 35 is equipped with means to insure that the intersection of the second saw cut with the first saw cut will be short of the far sides of the bone so that some bone cortex at that location is left intact. This significantly increases the changes of and rate of bone knitting after surgery. The means providing this feature of appliance 36 is an adjustable depth stop 46 mounted for movement along follower 36. The mounting arrangement for stop 46 preferably includes a pair of rods 47 secured to a base region 48 and slidingly received in passages provided therefor in guide pedestal 41. Stop 46 can be manipulated to position it at the desired location along follower 46 by means of a knob 49 attached to the free ends of rods 47. The position of stop 46 along follower 36 determines the extent to which follower 36 is permitted to penetrate the first saw cut 12. A set screw 50 carried by pedestal 41 is engageable with one of the rods 47 to lock the stop 46 in the desired position. If desired, follower 36 may have provided on one face thereof with distance marking indicia 51 to assist the surgeon in positioning stop 46. The depth of the osteotomy is usually determined in advance by the surgeon by other measurements of the bone. If desired, the initial mark 42 of indicia 51 may be positioned to give a false indication of the amount of follower 36 protruding in front thereof to insure that the apex of the osteotomy will be held back from the far side of the bone. For example, the one centimeter marking may be placed only one-half centimeter from the end of the follower 36.

To insure accuracy of the second cut 13 being made in bone 11, the guide 37 for the osteotome, indicated in phantom at 53 in FIG. 7, should be positioned closely adjacent bone 11. Inasmuch as the adjustable stop 46 for follower 36 has the effect of positioning track 39 at different distances with different bones, it is desirable that the mounting arrangement for guide 37 provide for radial reciprocal movement of the guide with respect to track 39 so that guide 37 can be moved up against the bone to be cut. The sliding mount for guide 37 is shown in FIGS. 5 and 7 and comprises a pair of rods 54 slidingly received in passages provided therefor in follower 42. A knob 55 can be provided at the free ends of rods 54 for manipulating the radial movement of guide 37 with respect to track 39. Another set screw 56 passing through follower 42 and engageable with one of the rods 54 is used to releaseably hold guide 37 in the position desired.

Figure 8:
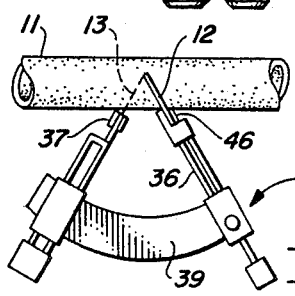
FIG. 8 is a diagramatic plan view of the appliance of FIG. 5 positioned to guide the second saw cut of an osteotomy on a small bone.
Figure 9:
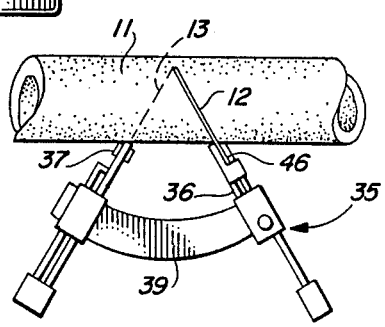
FIG. 9 is a view similar to FIG. 8, but showing the appliance in use with a larger bone.

FIGS. 8 and 9 illustrate the manner in which appliance 35 is manipulated when used with bones of different diameters. With a small bone, as shown in FIG. 8, stop 46 is positioned to allow only a small amount of follower 36 to enter the first saw cut 12 in bone 11. Guide 37 is positioned adjacent the surface of the bone in a position to guide the osteotome in making second saw cut 13 in such a manner that it intersects the apex of the first saw cut 12 short of the bone cortex on the far side of the bone. With a larger bone, as illustrated in FIG. 9, stop 46 is positioned to permit follower 36 to penetrate the proper distance into the first saw cut 12 and the adjustable mounting arrangement of guide 37 permits this member to be positioned adjacent the surface of the bone for guiding the second saw cut 13 in a manner to cause that second saw cut to intersect the first saw cut at the desired location.

From the foregoing it should be apparent that this invention provides a novel method and appliances for assisting a surgeon in performing an osteotomy with precisely placed and performed saw cuts in the bone.

What is claimed is:

1. An osteotomy appliance for the precision location of a second bone cut in angular relation to a first bone cut, comprising an elongated, blade-like follower adapted to be positioned within said first bone cut, said follower having a free end adapted to be inserted in said first bone cut generally in the direction of movement of the implement with which said first bone cut was made, a stop member mounted for adjustable movement lengthwise along said follower, said stop member being adapted to engage the bone when the follower is inserted into said first bone cut to limit the extent of penetration of said first bone cut by said follower, a saw guide movably connected to said follower and adapted to guide a saw blade along a predetermined path to make said second bone cut, and an arcuate track member connecting said saw guide and said follower and holding said guide in predetermined angular relationship to said follower.

2. The appliance of claim 1 including indicia on said follower to assist in positioning said stop member.

3. The appliance of claim 1 including indicia on said track member to assist in positioning said saw guide in relation to said follower.

4. The appliance of claim 1 wherein said track member is secured to said follower and said saw guide is slidably mounted on said track member.

5. The appliance of claim 1 further comprising means for mounting said saw guide for sliding movement along said arcuate track member and for reciprocal movement along a radius of said arcuate track member.

* * * * *